United States Patent [19]

Tubaro et al.

[11] Patent Number: 4,831,021

[45] Date of Patent: May 16, 1989

[54] GANGLIOSIDE DERIVATIVES

[75] Inventors: Ezio Tubaro; Giovanni Cavallo, both of Rome, Italy

[73] Assignee: Burroughs Wellcome Co., Research Triangle Park, N.C.

[21] Appl. No.: 123,763

[22] Filed: Nov. 23, 1987

Related U.S. Application Data

[63] Continuation of Ser. No. 632,200, Jul. 18, 1984, Pat. No. 4,728,641.

[30] Foreign Application Priority Data

Jul. 12, 1984 [IT] Italy .............................. 48724 A/83

[51] Int. Cl.$^4$ ............................................. A61K 31/70
[52] U.S. Cl. ................................... 514/54; 536/55.1; 536/55.3; 536/53; 536/123
[58] Field of Search ................ 514/54; 536/55.1, 55.3, 536/53, 123

[56] References Cited

U.S. PATENT DOCUMENTS

| | | | |
|---|---|---|---|
| 4,125,492 | 11/1978 | Cuatrecasas et al. | 536/55.1 |
| 4,415,733 | 11/1983 | Tayot | 536/55.1 |
| 4,464,360 | 8/1984 | Leffler et al. | 536/55.1 |
| 4,521,593 | 6/1985 | Martin | 536/55.3 |

FOREIGN PATENT DOCUMENTS 1269846  4/1972  United Kingdom .

OTHER PUBLICATIONS

Lundblad et al., "Eur. Jour. Biochem.," 104, pp. 323–330, 1980.
Leffler et al., "Fems. Microbiology Letters", 8, pp. 127–134, 1980.
Biochemistry, vol. 17, No. 13, 27th Jun. 1978, pp. 2619–2628, American Chemical Society; L. O. Sillerud et al., "Assignment of the 13c nuclear magnetic resonance spectrum of aqueous ganglioside GMI micelles".

Primary Examiner—Ronald W. Griffin
Attorney, Agent, or Firm—Donald Brown

[57] ABSTRACT

A novel mono-sialo ganglioside derivative substantially identical chemically and physically with a product prepared by
(a) concentration of an aqueous solution of a mono-sialo ganglioside and calcium ions under sub-atmospheric pressure at 40°–80° C. for 18–240 hours,
(b) adjustment of the pH to 2–3, followed by dialysis, and
(c) evaporation of the aqueous solvent.

The novel ganglioside is believed to be a new physical form of the known ganglioside $G_{M1}$ and shows activity against bacteria, viruses, protozoal, fungi and tumours. It has previously been suggested that gangliosides in general may be useful in the treatment of neurological disorders but not that they affect the activity of phagocytes.

5 Claims, 3 Drawing Sheets

FIG. 2

FIG.3

GANGLIOSIDE DERIVATIVES

This is a continuation of co-pending application Ser. No. 632,200, filed on July 18, 1984, now U.S. Pat. No. 4,728,641.

The present invention relates to novel ganglioside derivatives, pharmaceutical compositions containing such compounds, a method for preparing such compounds and compositions and a method of treating bacterial, viral, protozoal and fungal infections and tumors in mammals by administering such compounds and compositions.

The gangliosides are a class of naturally occurring glycosphingolipids which contain an oligosaccharide moiety to which may be attached one or more sialic acid groups. Gangliosides have been found in the brain, spleen, liver kidneys and blood of mammals and also in chicken eggs (see Ledeen, *J. Supramolecular Structure*, 8: 1-17 (1978) Cell Surface Carbohydrates and Biological Recognition 437–453 for a general review of the gangliosides).

The structure of ganglioside $G_{GNT}1$ has been reported (Wiegandt, *Angew Chemie internat. Edn.* 7. 87 (1968)) to be as follows:

wherein R is a sialic acid group.

According to the nomenclature proposed by Svennerholm (*J. Neurochem.*, 10, 613, 1963) the various gangliosides are designated by the letter G followed by one of four letters, M, D, T or Q depending on whether the ganglioside is a mono-, di-, tri- or tetra-sialo-ganglioside. These letters are followed by numerical indices allowing recognition of gangliosides containing the same quantity of sialic acid but having different chromatographic mobilities. These gangliosides may be positional isomers which can be distinguished by the use of a letter after the numerical index, for example ganglioside GM1b. Ganglioside $G_{M1}$ is the same as $G_{GNT}1$.

It has been postulated that gangliosides play a part in the normal functioning of the central nervous system (CNS) and it has been hypothesised (Miceli, Caltagirone and Gainotti, *Acta Psychiatra Scand.*, 1977, 55, 102) that gangliosides may exert a positive effect in the treatment of neuropathic syndromes. More recently it has been suggested (Spiegel, Ravid and Wilchek, *Proc. Natl. Acad. Sci., USA* 76, 5277, (1979)) that gangliosides are involved in lymphocyte stimulation in mammals. However, no suggestion has been made that gangliosides may affect the activity of phagocytes (polymorphonuclear leucocytes, macrophages, histiocytes, etc).

Polymorphonuclear leucocytes (PMNs) and macrophages (MCs) contstitute the major types of white blood cells and are responsible for combating infections, particularly bacterial and fungal infections, as well as preventing tumors spreading in mammals. Phagocytes normally act in the blood stream or at the site of infection via the blood stream.

It has now been discovered that certain gangliosides have an antibacterial, antiviral, antifungal, antiprotozoal and/or antitumor effect and can enhance the effect of antibacterial, antiviral, antifungal, antiprotozoal and/or antitumor agents in vivo.

The antibacterial, antiviral antifungal, antiprotozoal and/or antitumor effect observed when the gangalioside is administered alone is believed to be the result of the ganglioside increasing phagocytic activity.

Physical and chemical studies indicate that the gangliosides of the present invention, which are hereinafter referred as gangliosides $G_{M1}P$, have the same chemical structure but a different physical form compared with the naturally occurring gangliosides. It is believed that gangliosides $G_{M1}P$ aggregate in a different manner from the naturally occurring gangliosides $G_{M1}$ from which $G_{M1}P$ is derived.

Accordingly, the present invention provides a mono-sialo ganglioside $G_{M1}P$ characterised in that it is substantially identical in terms of its chemical structure and physical nature to a product prepared from a mono-sialo ganglioside by the following process:

(1) concentration of an aqueous solution containing a mono-sialo ganglioside and calcium cations under vacuum at a temperature between 40° C. and 80° C. for between 18 and 240 hours, (2) adjustment of the pH to between pH2 and 3 followed by dialysis, and (3) evaporation of the aqueous solvent.

The present invention also provides a mono-sialo ganglioside $G_{M1}P$ prepared by the process described above, the process for preparing such ganglioside derivatives, and a mono-sialo ganglioside $G_{M1}P$ obtainable from such a process.

The mono-sialo gangliosides suitable for derivatisation according to the present invention include those of the formula (I):

(I)

wherein *either* $R^1$ is a group $-CH_2-CH(NHCOR^4)-CH(OH)-CH=CH(CH_2)_nCH_3$ wherein n is 12 or 14, $R^4$ is a $C_{15}-C_{23}$ aliphatic chain, such as $(CH_2)_{16}CH_3$ and $R^2$ and $R^3$ are one of the following combinations:

$R^2=OR^5$ ($R^5$ being N-acetylneuraminic acid), and $R^3$=galactose (linked at the 1-position) (ganglioside $GM_1$);

$R^2=OR^5$, and $R^3$ =H(ganglioside $GM_2$);

$R^2=OR^5$ and $R^3$=fucose;

$R^2=OR^6$ ($R^6$ being glycolylneuraminic acid) and $R^3$=H, galactose or fucose;

$R^2$=OH and $R^3$=galactose (asialo ganglioside GM1) *or* $R^1$ is H, $R^2$ is as defined above and $R^3$ is $-CH_2CH(NHCOR^4)CH(OH)CH=CH(CH_2)_nCH_3$ wherein $R^4$ and n are as defined above (ganglioside $G_{M_1}b$)

Preferably the compounds of the formula (I) contain an N-acetylneuraminic acid or N-glycolylneuraminic acid group. It has been found that poly-sialo gangliosides readily hydrolyse thermally to give the corresponding mono-sialo gangliosides. In particular poly-sialo gangliosides hydrolyse at the temperatures used to prepare the products of the present invention. Thus, the mono-sialo ganglioside used in the preparation of the products of the present invention is suitably a mono-sialo ganglioside obtained commercially as a mono-component ganglioside or in a mixture of gangliosides (for example ganglioside $G_{III}$ obtained from Sigma) or in the form of material extracted from natural sources (brain, blood, blood cells, etc) that contains gangliosides, for example acetonic powder (obtained by conventional methods) or freeze-dried brain obtained from the brains of animals, conveniently ox brains, or is formed in situ from one or more poly-sialo gangliosides under the conditions of step 1 of the process for preparing products of the present invention.

The gangliosides used in the preparation of the products of the present invention are suitably in a substantially pure form (ie, less than 50%, suitably less than 20% and preferably less than 10% of impurities) which may be obtained by conventional purification methods used to purify gangliosides such as column chromatography (see example L. Svennerholm, Methods in Carbohydrate Chemistry, 6, 464–474).

The aqueous solution in step 1 above is preferably prepared by the simple admixture of the ganglioside with an aqueous solution containing calcium ions (such as an aqueous solution of calcium chloride) to give a calcium ion concentration of between 1 and 10 mM (preferably about 5 mM) followed by thorough mixture. Alternatively, the aqueous solution may be prepared by dialysis of the ganglioside against an aqueous solution containing calcium cations (such as an aqueous solution containing calcium bicarbonate) in order to achieve a calcium ion concentration of 1 to 10 mM (preferably about 5 mM). The dialysis is suitably carried out for a period between 24 and 72 hours, conveniently 48 hours. The water used in this dialysis may be either natural water or distilled water which contains calcium cations or distilled water to which such ions have been added. Prior to concentration of the aqueous solution a minor proportion of a $C_{1-4}$ alkanol, preferably methanol, is conveniently added to the solution. It has been found that the addition of 25% v/v methanol (relative to the volume of the total solution) is particularly convenient in the case where the aqueous solution is prepared by dialysis, the methanol being preferably added after the dialysis.

In the concentration step, the volume of the solution being concentrated is conveniently kept constant by the continuous addition of further solution containing ganglioside and calcium cations to replace water distilled off. The total volume of the aqueous solution is reduced thereby by a factor of between 10 and 40 in a typical preparation. A vacuum is conveniently applied (suitably between 20 and 50 mm Hg) and the internal temperature maintained between 55 and 80° C., suitably 59.5° C., using an external temperature range of between 60° and 90° C., suitably 67.5° C. The concentration procedure is thereby preferably continuous and linearly progressive.

Suitably, the concentration is completed in less than 110 hours. When the concentration is carried out on an aqueous solution having a temperature of 59.5° C., the concentration process is conveniently carried out for about 55 hours.

The pH of the concentrated solution is adjusted in Step 2 with organic or mineral acids to a preferred pH of about 2.6. The acid used is conveniently HCl, suitably 6 N. HCl. Suitably, the dialysis is carried out against distilled water or a dilute acid solution having a pH of about 2.6 (a dilute hydrochloric acid solution is preferred) followed by dialysis against distilled water. The distilled water is suitably redistilled before use. Suitably this dialysis is carried out at a temperature of between 1 and 10° C., conveniently 4° C., for about 24–72 hours, conveniently 48 hours.

The evaporation of the aqueous solvent in step 3 is carried out by conventional methods well known to those skilled in the art, for example by the technique known as freeze-drying i.e. by freezing the aqueous solution and evaporating the water off under vacuum.

The ganglioside $G_{M_1}P$ of the present invention will normally contain less than 80%, suitably less than 50%, most suitably less than 20% and preferably less than 5%, of impurities, such as ganglioside $G_{M_1}$, other gangliosides or other derivatives thereof. The ganglioside $G_{M_1}P$ of this invention may be separated from underivatised gangliosides by dialysis of an aqueous suspension of a mixture of derivatised and underivatised gangliosides that contains a minor proportion of methanol against distilled water and freeze drying the resultant suspension.

Figure 2:
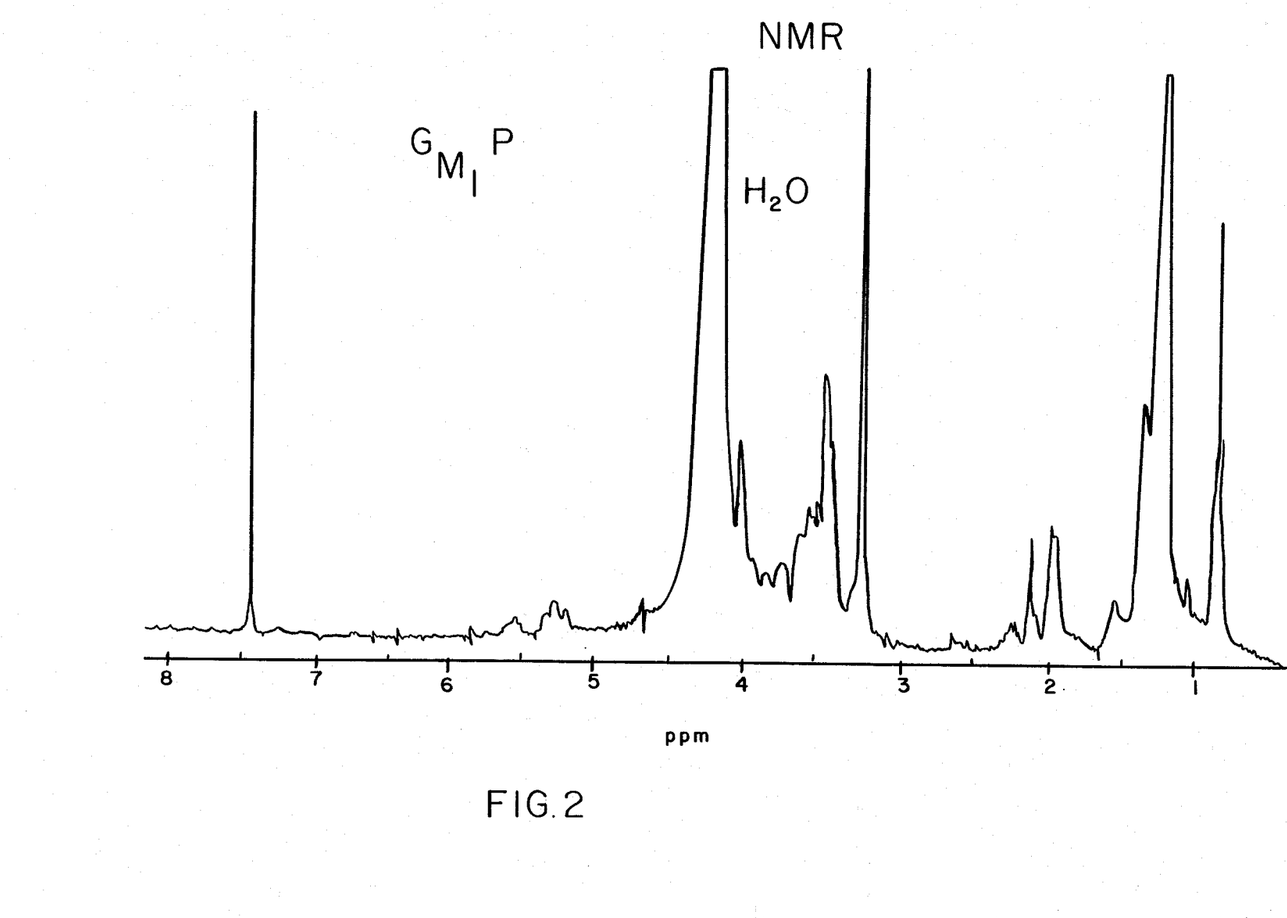

A ganglioside $G_{M_1}P$ according to the present invention has been found to have an Rf value of 0.245 (compared to an Rf of 0.31 for ganglioside $G_{M_1}$) by thin layer chromatography (substrate: Merck Silica Gel 60 F254, heated to 110° C. for 30 minutes, plate thickness: 0.25 mm, eluant: chloroform/methanol/water, 55/45/10; plate saturated for one hour before elution) although it has also been found that this value approaches the value for $GM_1$ as the purity of the $GM_1P$ increases. It gives a positive reaction when sprayed with sulphuric acid (concentrated sulphuric:water, 1:1) with resorcinol reagent, with orcinol/FeCl₃, and with other typical reagents for detection of gangliosides, but little reaction when sprayed with ninhydrin (0.2% in ethanol). It has an nmr spectrum substantially as shown in FIG. 2.

Accordingly, the present invention provides a ganglioside $G_{M1}P$ characterised in that:
(a) by thin layer chromatography
  (i) it gives a positive reaction to sulphuric acid reagent (concentrated sulphuric acid:water, 1:1), resorcinol reagent, orcinol/FeCl₃ and other typical reagents for ganglioside detetection,
  (ii) it gives little reaction to ninhydrin reagent (0.2% ninhydrin in ethanol),
(b) it has, when in aqueous solution, a $^{13}C$ n.m.r. spectrum substantially indentical to that shown in FIG. 2,
(c) it has in vivo activity in mice against *Klebsiella pneumoniae* when tested by the method described hereafter, and
(d) it has in vivo activity in mice against Herpes HSV-1 (strain F) when tested by the method described hereafter.

Figure 1:
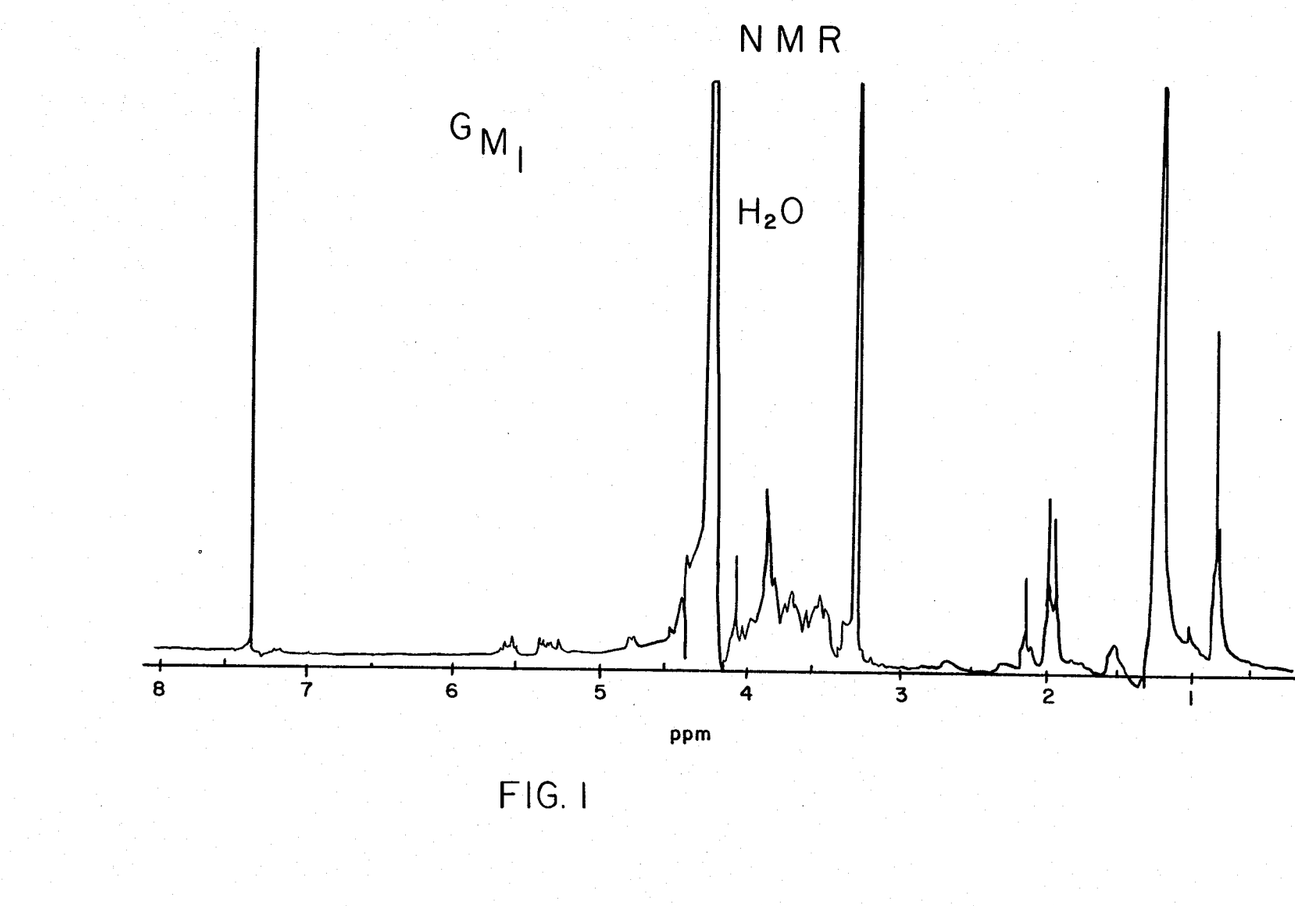

From a comparison of the $^{13}C$ n.m.r. spectra of the mono-sialo ganglioside $GM_1$ (FIG. 1) in water and the product of the present invention $G_{M1}P$ (FIG. 2) it is apparent that the major differences in the spectra are that many of the peaks from $G_{M1}P$ are much broader than the corresponding peaks from $G_{M1}$ (NB the spectra shown have been smoothed with a digital filter whose line-width is the same as the average peak width in each case). It is believed that these differences are the result of modifications in the way that the ganglioside molecules are associated with each other, both in the solid state and in water. It is well known that gangliosides aggregate in water e.g. M. Corti, V. Degiorgio, R. Ghidoni, S. Sonnino and G. Tettamanti, Chemistry and Physics of Lipids 26 (1980) 225-238.

It is also believed that there are no chemical differences between $G_{M1}P$ and $G_{M1}$ as the $^{13}C$ n.m.r. spectra of a mixture of $G_{M1}P$ and $G_{M1}$ in solution in chloroform:methanol:water 60:34:6 v/v shows only one set of peaks.

The ganglioside $G_{M1}P$ may also be distinguished from the naturally occurring ganglioside $G_{M1}$ on the basis of their optical activities, for example by circular dichroism measurement, and by differential calorimetry.

The present invention also provides a pharmaceutical composition comprising a ganglioside $G_{M1}P$, as hereinbefore defined, together with a pharmaceutically acceptable carrier. The amount of ganglioside present in such a composition will normally be between 0.05 and 100 mg, suitably between 0.5 and 10 mg and conveniently 1 mg. The dose of the ganglioside administered will normally be between 0.1 and 500 mg, suitably 0.5 and 50 mg, conveniently 0.5 to 10 mg per man per day per week. The precise dose will, of course, vary with the condition of the patient and the route of administration. It is believed that the pharmaceutical compositions of the present invention may be used, for example, before operations to help alleviate the immunodepressant effects of certain anaesthetics (halothane, etc); prophylatically to improve the cellular defence of children during epidemics; after viral infections to prevent the development of bacterial and fungal infections and tumors; and in the treatment of immunodepression, e.g. to counteract the immunodepressant effect of cytostatic drugs given to patients. The ganglioside $G_{M1}P$ may also usefully be combined with other active agents and administered in the form of suitable pharmaceutical compositions.

Accordingly, the present invention provides a pharmaceutical composition for increasing resistance to bacterial, viral, fungal and protozoal infections and tumors, particularly bacterial infections, in mammals, the composition comprising a mono-sialo ganlioside $G_{M1}P$ as hereinbefore defined in combination with an antibacterial, antiviral antiprotozoal, antifungal and/or antitumor agent or in combination with a substance which depresses or enhances the activity of phagocytes in mammals, together with a pharmaceutically acceptable carrier.

Suitable antibacterial agents include benzylpyrimidines, tetracyclines, β-lactam antibiotics such as the penicillins and the cephalosporins, those antibiotics containing sugar components such as the aminoglycoside antibiotics, and sulphonamides.

Trimethoprim, diaveridine and tetroxoprim are particularly well known examples of benzylpryimidines which have an antibacterial effect, but other benzylpyrimidines in which the phenyl group is substituted by one or more substituents, preferably three substituents, are also suitable for inclusion within the compositions of the present invention. Suitable substituents include $C_{1-4}$ alkoxy groups, including those containing an additional oxygen atom in the carbon chain such as methoxyethoxy, $C_{1-4}$ alkyl groups, $C_{2-4}$ alkenyl groups, $C_{1-4}$ alkylthio groups, halogen atoms, amino groups optionally substituted by one or two $C_{1-4}$ alkyl groups and other substituents well known in the art.

Suitable tetracyclines include tetracycline, oxytetracycline, doxycycline, chlortetracycline, demethylchlortetracycline and tetracycline phosphate complex.

Suitable pencillins include the naturally occurring penicillins and the semisynthetic pencillins, such as those which contain an acylamino side-chain attached to the 6-position of the penicillin nucleus. Ampicillin, amoxycillin, azidocillin, talampicillin, carbencillin, ticarcillin, piperacillin, oxacillin, azlocillin, mezocillin, hetacillin, flucloxacillin, cloxacillin and benzylpenicillin are particularly suitable penicillins for inclusion within the compositions of the present invention.

Suitable cephalosporins include those formed as fermentation products such as cephalosporin C and those prepared semi-synthetically such as those containing an acylamino side chain at the 7-position of the cephalosporin nucleus, for example cephadine, cephoxitin, cephamandole, the cephamycins, cephaloridine, cephalexin, cephalathin, cephuroxime, cephaloglycin and cephaprim sodium.

Other β-lactam antibiotics have been thoroughly reviewed in the art. Examples of particularly suitable aminoglycoside antibiotics for inclusion within the compositions of the present invention are streptomycin, erythromycin, carbomycin, the kanamycins, amicetin, gentamycin and oleandomycin.

Suitable sulphonamides for inclusion within the compositions of the present invention include sulfanilamide, sulfadiazine, sulfamethisazole, sulfapyridine, sulfathiazole, sulfamerazine, sulfamethazine, sulfioxazole, sulformethoxine, 2-(p-aminobenzene(sulfonamide-3-methoxypyrazine (Kelfizina), p,p¹-Diamino-diphenylsulfone, amino-p-toluenesulfonamide, 5-sulfanilamido-2,4-dimethyl pyrimidine, 4-(N¹-acetylsulfanilamido)-5,6-dimethoxy pyrimidine, 3-sulfanilamido-4-5-dimethylisoxazole, 4-sulfanilamido-5-methoxy-6-decyloxy pyrimidine sulfamonomethoxine, 4-p-(9-hydroxyquinilinyl-4-azo)-phenyl sulfanilamido-5,6-dimethoxy pyrimidine, sulfadimethoxine, sulfadimidine, sulfamoxole, sulfadoxine, sulfaguanidine, sulfathiodimethoxine, sulfamethoxazole, sulfaquinoxaline, and p-(2-methyl-8-hydroxy-quinolinyl-5-azo)-phenyl sulfanilamido-5,6-dimethoxy pyrimidine.

A particularly suitable antiviral agent for use in combination with the mono-sialo ganglioside $G_{M1}P$ of the present invention is acyclovir.

Substances which depress the activity of phagocytes in mammals and are therefore suitable for inclusion in the pharmaceutical compositions of the present inventions are well documented in the literature. Such substances include cytostatic agents, for example adriamycin and the alkylating agents (e.g. cyclophosphamide) and vinca alkaloids, and corticosteroids, for example beta-methazone.

Similarly, substances which enhance the activity of phagocytes in mammals and are therefore suitable for inclusion in the pharmaceutical compositions of the present invention are well documented in the literature. Such substances include pyran copolymer, glucan muramyldipeptide, lentinan, tuftsin, CP and BCG etc.

One group of preferred pharmaceutical compositions of the present invention comprises a mono-sialo ganglioside $G_{M1}P$ as hereinbefore defined together with an antibacterial agent and a pharmaceutically acceptable carrier. Particularly preferred antibacterial agents include the benzylpyrimidines, for example trimethoprim, the tetracyclines, for example tetracycline, the aminoglycoside antibiotics, the example gentamycin, and the semi-synthetic pencillins, for example ampicillin, and the cephalosporins.

A further group of preferred pharmaceutical compositions of the present invention comprises a ganglioside $G_{M1}P$ as hereinbefore defined together with a substance which depresses or enhances the activity of phagocytes in mammals in combination with a pharmaceutically acceptable carrier.

A yet further group of preferred pharmaceutical compositions comprises a mono-sialo ganglioside $G_{M1}P$ as hereinbefore defined together with an antibacterial agent which depresses the activity of polymorphonuclear leucocytes in mammals in combination with a pharmaceutically acceptable carrier. The tetracyclines are examples of such antibacterial agents.

A still further group of preferred pharmaceutical compositions comprises monosialo ganglioside $G_{M1}P$ as hereinbefore defined together with an antiviral agent, such as acyclovir. A still further group of preferred pharmaceutical compositions comprises monosialo ganglioside $G_{M1}P$ as hereinbefore defined together with an antiprotozoal agent, such as pyrimethamine.

The ratio of the mono-sialo ganglioside derivative to the second active component of the composition will normally be from 100:1 to 1:500 and suitably 1:1 to 1:100 by weight.

The exact weight ratio of the mono-sialo ganglioside derivative to the second active component will vary with the particular second active component being incorporated into the compositions.

The optimum dose of the mono-sialo ganglioside derivative and second active component will, or course, vary with the nature of the second component, the condition of the patient and the route of administration, but the dose of the mono-sialo ganglioside derivative will normally be from 0.01 mg to 500 mg and preferably 0.1 mg to 10 mg per man per day (0.001 to 0.1 mg/kg body weight per day). The combination of the ganglioside with the second active component will normally be given in a dose of 0.1 mg to 500 mg, suitably 1 to 100 mg and preferably 1 mg to 50 mg per man per day.

The pharmaceutically acceptable carrier will of course, be "acceptable" in the sense of being compatible with the other ingredients of the composition and not deleterious to the recipient of the composition. The carrier may be solid or a liquid, or a mixture of solid and liquid substances, and may be formulated with other components of the composition as a unit dose, for example a tablet, capsule, or sachet for oral administration or a suppository for rectal administration. Other pharmaceutically active substances may also be included in compositions of the present invention, and the composition may be formulated by any of the well known techniques of pharmacy, consisting basically of admixture of its components. Unit dose formulations for oral, rectal or parenteral administration conveniently contain a combination of the ganglioside $G_{M1}P$ derivative and the second active component of the composition in an amount in the range 0.1 to 500 mg, preferably 1 to 50 mg.

For oral administration, fine powders or granules of the components may contain diluents and dispersing and surface active agents, and may be presented in a draught in water or in a syrup, in capsules or sachets in the dry state, or in an aqueous or non-aqueous suspension, when a suspending agent may also be included; in tablets, preferably made from granules of the active ingredient with a diluent, by compression with binders and lubricants; or in a suspension in water or a syrup or an oil or in a water/oil emulsion, when flavouring, preserving, suspending, thickening and emulsifying agents may also be included. The granules or the tablets may be coated and the tablets may be scored.

For parenteral administration (by intravenous, intraperitoneal or subcutaneous administration) the composition of the present invention may be presented in unit dose or multi-dose containers in aqueous or non-aqueous injectable solutions which may contain anti-oxidants, buffers, bacteriostats and solutes which render the compounds isotonic with the blood; or in aqueous or non-aqueous suspensions when suspending and thickening agents may be included; extemporaneous injection solutions and suspensions may be made from sterile powders, granules or tablets which may contain diluents, dispersing and surface active agents, binder and lubricants. The solvents used in these compositions will be solvents which are not deleterious to the stability of the mono-sialo ganglioside derivative. Preferred solvents include water, saline and EDTA. Organic solvents such as the glycols, particularly ethylene and propylene glycol, may often be incorporated in the injectable solutions of the present invention.

When water is the solvent vehicle, a buffer will also normally be present. Saline is the preferred solvent.

The compositions may also take the form of two part packs, the parts being mixed prior to administration. In such a two part pack the ganglioside $G_{M1}P$ will conveniently be present as a freeze-dried solid.

It is preferred to administer parenterally the compositions of the present invention.

It may often be desirable to administer a dose of the mono-sialo ganglioside $G_{M1}P$ prior to the administration of the composition of the present invention that contain a second active ingredient. Thus, the present invention also provides a pack containing at least one unit dose of the mono-sialo ganglioside $G_{M1}P$ as hereinbefore defined and at least one unit dose of a composition of the present invention containing a second active ingredient as hereinbefore defined, the separate unit doses being clearly labelled, together with instructions for ensuring that the doses are administered in the correct order.

The compositions of the present invention, and the mono-sialo ganglioside $G_{M1}P$, may be used for the treatment or prophylaxis of bacterial, viral, protozoal and fungal infections and tumors in mammals. The composition and the mono-sialo ganglioside $G_{M1}P$ are preferably used for the prophylaxis of bacterial, viral, protozoal and fungal infections and to prevent tumors spreading in mammals.

Thus, the present invention provides a method for the treatment or prophylaxis of bacterial infections in mammals which comprises the administration of an antibacterially effective non-toxic amount of mono-sialo ganglioside $G_{M1}P$ as hereinbefore defined to mammals.

The present invention also provides a method for the treatment or prophylaxis of viral infections which comprises the administration of an antivirally effective amount of a mono-sialo ganglioside $G_{M1}P$ as hereinbefore defined to mammals.

The present invention also provides a method for the treatment or prophylaxis of fungal infections and tumors in mammals which comprises the administration of an anti-fungally effective non-toxic amount of a mono-sialo ganglioside $G_{M1}P$ as hereinbefore defined to mammals.

The present invention also provides a method for the treatment or prophylaxis of protozoal infection in mammals which comprises the administration of an anti-protozoally effective non-toxic amount of a mono-sialo ganglioside as hereinbefore defined to mammals.

The present invention also provides a method for the treatment or prophylaxis of tumors in mammals which comprises the administration of an anti-tumorally effective non-toxic amount of mono-sialo ganglioside $G_{M1}P$ as hereinbefore defined to mammals.

It is believed that mono-sialo ganglioside $G_{M1}P$ as hereinbefore defined has not previously been disclosed as having any medical utility. The present invention, therefore, also provides a mono-sialo ganglioside derivative, as hereinbefore defined, for use in medicine and, in particular, for the treatment of bacterial, viral, protozoal or fungal infections or tumors in mammals. The following examples illustrate the preparation of the gangliosides $G_{m1}P$, their pharmacological properties and pharmaceutical compositions containing them.

EXAMPLE 1

Preparation of ganglioside $G_{M1}P$ (i) Fresh grey matter (1 kg) from ox brain was homogenised with acetone (3 l) and the resultant suspension filtered under vacuum. The residue was mixed with acetone (1 l) and homogenised and filtered as before. The solid residue of acetone dried powder was dried under air-flow at room temperature for 18 hours. Typical yield of acetone dried powder was 150–200 g/kg of grey matter.

(ii) The triturated acetone dried powder (19.2 g) from ox-brain was added to a chloroform/methanol mixture (2,100 ml, 1:1). The mixture was shaken vigorously for one hour and then filtered. Chloroform (1,050 ml) and 0.1M potassium chloride solution (625 ml) were added to the filtrate.

The mixture was shaken for a further hour and then allowed to stand overnight. The upper phase of about 1,270 ml, which had settled out on standing, was separated and dialysed against redistilled water at 15° C. for 48 hours in a Visking tube.

(iii) The aqueous solution after dialysis was freeze-dried and the freeze-dried powder taken up in redistilled water and dialysed again for 48 hours. The aqueous solution was freeze-dried and the resultant product chromatographed on a silica gel column by the method of Svennerholm (Methods in Carbohydrate Chemistry, 6, 464–474), eluting with a chloroform-methanol-water mixture. The fractions containing ganglioside $GM_1$ were pooled and freeze-dried.

The freeze-dried product was taken up in redistilled water and dialysed against running tap water at 15° C. for 48 hours in a Visking tube (9.5 cm diameter, 110 cm length). An aqueous solution of calcium bicarbonate in distilled water (calcium ion concentration about 200 $\mu$g/ml) can be used as a replacement for tap water.

Figure 3:
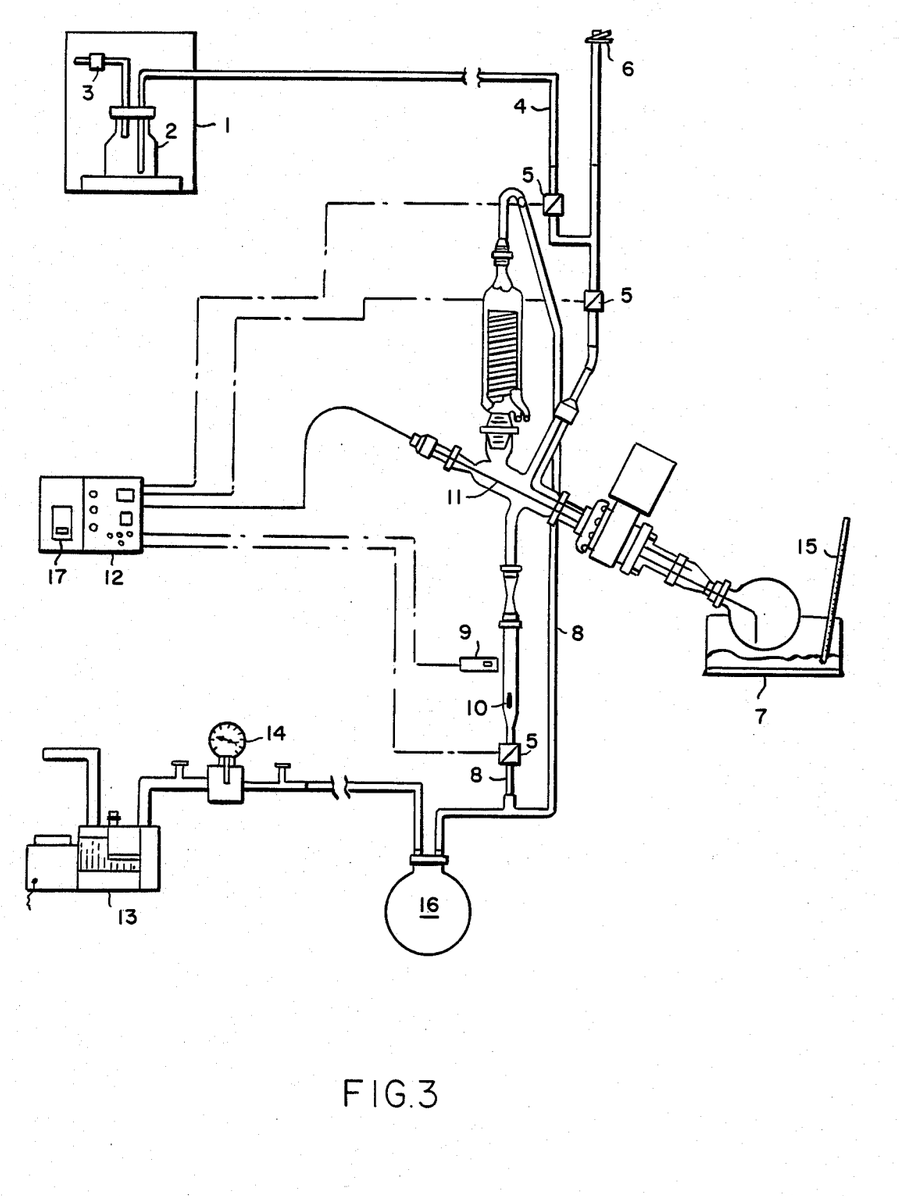

(iv) An aqueous solution of the mono-sialo ganglioside was concentrated by continuous evaporation under vacuum using the evaporator shown in FIG. 3. 200 ml of the aqueous solution was placed in the round-bottomed flask and the flask heated at a bath temperature of 67.5° C. (internal temperature 59.5° C.). The water which distilled off under vacuum was replaced continuously by further aqueous ganglioside solution from the flask (2) by means of a sensor (9) and automatic valve (5) adjusted to respond to signals from the sensor such that the same volume of liquid is added to the flask via the valve (5) as is evaporated and passes through the sensor (9) as condensate.

(v) The pH of the concentrated ganglioside solution (200 ml) was adjusted to pH 2.6 by the addition of concentrated (50%) hydrochloric acid. The resultant solution was dialysed against running redistilled water (100 l) for 48 hours under magnetic stirring at 4° C. in a Visking tube (4.5 cm diameter, 160 cm length). The solution so obtained was lyophilised on standard freeze-drying apparatus. The yield was between 95 and 100 mg from 19.2 g acetone dried powder.

EXAMPLE 2

The procedure of Example 1 was repeated up to the end of part (iv). The pH of the concentrated ganglioside solution (200 ml) was then adjusted to pH 2.6 by the addition of concentrated (50 %) hydrochloric acid. The resultant solution was dialysed against an aqueous solution of hydrochloric acid (pH 2.6) using an Amicon Membrane System (membrane U5UMO5 of 500 M. W. and 62 mm diameter until the effluent from the dialysis had a pH of 2.6 (this occurred after about 18 hours). The acidic solution was dialysed against distilled water in Visking tubing as in Example 1 and the solution so obtained was lyophilised on standard freeze-drying apparatus.

Biological Activity of the Ganglioside Derivatives of the Present Invention

1. Against *K. pneumoniae*

Swiss male albino mice (Charles river CDI) weighing 20 ±1g were randomised and divided into two groups of 20 animals each. The mice were injected intraperitoneally with 0.25 ml/10 g mouse with a 24 hour broth culture of *Klebsiella pneumoniae* CN 3632 in brain-heart broth (Difco) which had been centrifuged, washed with saline and then resuspended in saline to obtain $2 \times 10^7$ micro-organisms/ml. One group of 20 mice had previously had 2.5 mg/kg of ganglioside $G_{M1}P$ obtained by the method of Example 2 herein administered intravenously 24 hours before *K. pneumoniae* infection. The results on the eighth day after infection were as follows:

| Group | Mortality Death | % Mortality |
|---|---|---|
| Controls | 16/20 | 80 |
| Ganglioside $G_{M1}P$ | 0/20 | 0 |

2. Against Herpes HSV-1 (strain F) virus

BALB/c mice weighing 16 g were randomised into three groups of 6 animals each. The mice were injected intraperitoneally with $2.5 \times 10^{10}$ pfu/ml (12 LD$_{50}$) of HSV-1 (strain F) virus provided by Dr. B. Roizman of the University of Chicago. Two groups of mice had 0.6 mg/kg and 3 mg/kg respectively of $G_{M1}P$ obtained by the method of Example 2 herein administered intraperitoneally twice daily commencing 48 hours before infection until the seventh day after infection. The animals of the third group, which acted as controls, were injected with the same volume of solvent at the same times as the treated animals.

| Group | Survival time of each mouse in hours | M.S.T. (hours) | No. of survivors at day 7 |
|---|---|---|---|
| 1 | 12,12,12,24,24,36 | 20 | 0/6 |
| 2 | 180,192,288,288,288 | 254 | 4/6 |
| 3 | 180,192,288,288.288.288 | 254 | 4/6 |

Group
1 = controls
2 = 0.6 mg/kg ganglioside GM$_1$ derivative
3 = 3 mg/kg ganglioside GM$_1$ derivative
M.S.T. = Mean survival time 3. Against Plasmodium berghei protozoa 40 Swiss male albino mice (Charles River CD1) weighing $22 \pm 1$ g were randomly divided into groups of 10 and injected intraperitoneally with 0.1 ml/10 g of citrated blood of 6-day parasitised mice which had been diluted 1:1000 (v/v) with saline to obtain $1.58 \times 10^6$ *P. berghei* I.S.S./ml. The control group (1) were injected with saline, group 2 with ganglioside $G_{M1}P$ prepared by the method of Example 1 (5 mg/kg s.c. in saline), group 3 with the known anti-protozoal agent pyrimethamine (1 mg/kg s.c. in CMC 0.25% in water, w/v), and group 4 with both $G_{M1}P$ and pyrimethamine at the doses stated above. The dose volume was 0.25 ml/10 g. The $G_{M1}P$ was administered 24 hours and 2 hours before infection (Day 0) and the pyrimethamine on days 0, 1 and 2.

The results were as follows:

| Group | Mortality (%) Day 9 | Day 13 |
|---|---|---|
| 1 | 100 | (100) |
| 2 | 90 | 100 |
| 3 | 50 | 90 |
| 4 | 20 | 80 |

Thus, $G_{M1}P$ is shown to have an anti-protozoal effect and also to enhance the efficacy of a standard anti-protozoal agent.

4. Against Candida Albicans

53 Swiss male albino mice (Charles River CD1) weighing $23 \pm 1$ g were randomly divided into two groups of 10, 14, 14 and 15 amimals each (groups 1 to 4 respectively). Group 1 animals were injected with saline as a control group; Group 2 were injected with cyclophosphamide 50 mg/kg (0.2 ml/mouse) intravenously 96 hours before infection; Group 3 with cyclosphosphamide 50 mg/kg (0.2 ml/mouse) intravenously 96 hours before infection and with GM$_1$P 10 mg/kg (0.25 ml/10 g) subcutaneously at 96 and 24 hours before infection; and Group 4 with $G_{M1}P$ 10 mg/kg (0.25 ml/10 g) subcutaneously 96 and 24 hours before infection. The mice were then injected intravenously with 0.225 ml/mouse of an 18 hour culture of Sabouraud glucose broth containing $1.204 \times 10^7$ *Candida Albicans* cells/ml (strain CN 7996).

The results were as follows:

| Group | Mean survival time (days) | Number alive at Day 23 |
|---|---|---|
| 1 | 8.00 | 0 |
| 2 | 1.21 | 0 |
| 3 | 6.28 | 0 |
| 4 | 12.06 | 3 |

These results show that GM$_1$P has an antifungal action and also that it reverses to some extent the immunosuppressant activity of cyclophosphamide.

Toxicity

Ganglioside $G_{M1}P$ obtained from Example 2 herein was injected intraperitoneally into mice to a maximum dose of 30 mg/kg. No toxic effects were observed.

What we claim is:

1. A ganglioside $G_{M1}P$ compound characterized in that:
   (a) by thin layer chromatography
      (i) it gives a positive reaction to sulphuric acid reagent (concentrated sulphuric acid:water, 1:1), resorcinol reagent, orcinol/FeCl$_3$ and other typical reagents for ganglioside detection,
      (ii) it gives little reaction to ninhydrin reagent (0.2% ninhydrin in ethanol),
   (b) it has, when in aqueous solution, a $^{13}$C n.m.r. spectrum substantially identical to that shown in FIG. 2,
   (c) it has in vivo activity ink mice against Klebsiella pneumoniae, and
   (d) it has in vivo activity in mice against Herpes HSV-1 (strain F) in said mammal.

2. A pharmaceutical composition comprising a ganglioside $G_{M1}P$ compound characterized in that:
   (a) by thin layer chromatography
      (i) it gives a positive reaction to sulphuric acid reagent (concentrated sulphuric acid:water, 1:1), resorcinol reagent, orcinol/FeCl$_3$ and other typical reagents for ganglioside detection,
      (iii) it gives little reaction to ninhydrin reagent (0.2% ninhydrin in ethanol),
   (b) it has, when in aqueous solution, a $^{13}$C n.m.r. spectrum substantially identical to that shown in FIG. 2, (c) it has in vivo activity in mice against *Klebsiella pneumoniae*, and (d) it has in vivo activity in mice against Herpes HSV-1 (strain F) in said mammal, together with a pharmaceutically acceptable carrier therefor.

3. A method of treating a tumor in a mammal comprising the administration to said mammal of an effective antitumor amount of the compound of claim 1.

4. The composition of claim 2 in a form for parenteral administration.

5. The composition of claim 2 in a tablet or capsule form for oral administration.

* * * * *

UNITED STATES PATENT AND TRADEMARK OFFICE
CERTIFICATE OF CORRECTION

PATENT NO. : 4,831,021

DATED : May 16, 1989

INVENTOR(S) : Ezio Tubaro et al

It is certified that error appears in the above-identified patent and that said Letters Patent is hereby corrected as shown below:

On the title page, priority date "July 12, 1984" should read --- July 21, 1983 ---.

Signed and Sealed this

Twenty-fourth Day of April, 1990

Attest:

HARRY F. MANBECK, JR.

*Attesting Officer*   *Commissioner of Patents and Trademarks*